United States Patent
Iwasaki et al.

[11] Patent Number: 5,970,163
[45] Date of Patent: *Oct. 19, 1999

[54] PROCESS FOR VISUALLY MEASURING A MICROBIAL ACTIVITY STATE DURING REAL TIME

[75] Inventors: Hiroshi Iwasaki, Hirakata; Tomoaki Fukushige; Hirofumi Akano, both of Handa; Satoshi Nomura; Katsuhiko Tomita, both of Miyanohigashi-machi, all of Japan

[73] Assignee: Horiba, Ltd., Kyoto, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/660,687

[22] Filed: May 31, 1996

[30] Foreign Application Priority Data

May 31, 1995 [JP] Japan ................................. 7-156925

[51] Int. Cl.⁶ ..................................................... G06K 9/00
[52] U.S. Cl. ......................... 382/128; 422/82.05; 435/41; 436/68
[58] Field of Search .................................. 382/128–134; 435/39, 41, 287.3; 356/39; 422/82.02, 82.05; 436/68

[56] References Cited

U.S. PATENT DOCUMENTS

| | | | |
|---|---|---|---|
| 5,117,467 | 5/1992 | Misaki et al. | 382/133 |
| 5,188,946 | 2/1993 | Ward, Jr. et al. | 435/39 |
| 5,257,182 | 10/1993 | Luck et al. | 382/224 |
| 5,290,701 | 3/1994 | Wilkins | 435/287.3 |
| 5,292,456 | 3/1994 | Francis et al. | 252/628 |
| 5,389,544 | 2/1995 | Sugata et al. | 435/39 |
| 5,473,706 | 12/1995 | Bacus et al. | 382/133 |
| 5,500,188 | 3/1996 | Hafeman et al. | 422/82.02 |
| 5,510,244 | 4/1996 | Inoue et al. | 435/39 |
| 5,510,246 | 4/1996 | Morgan | 435/39 |
| 5,526,258 | 6/1996 | Bacus | 382/129 |
| 5,567,598 | 10/1996 | Stitt et al. | 435/39 |
| 5,616,162 | 4/1997 | Crawford et al. | 71/9 |

FOREIGN PATENT DOCUMENTS 9426870 11/1994 WIPO .

OTHER PUBLICATIONS

"Rapid Dectection of *E. coli* Immobilised in Gel Microdroplets," by by Williams et al., Annals of the New York Academy of Sciences 501 (1987).

"Improvement of Spatial Resolution of a Laser–Scanning pH–Imaging Sensor," by Nakao et al., Jpn. J. Appl. Phys. vol. 33 (1994) pp. L394–L397, Part 2, No. 3A, Mar. 1, 1994.

"Scanning–laser–beam semiconductor ph–imaging sensor," Nakao et al., Sensors and Actuators B, 20 (1994), 119–123.

*Primary Examiner*—Amelia Au
*Assistant Examiner*—Jayanti K. Patel
*Attorney, Agent, or Firm*—Price Gess & Ubell

[57] ABSTRACT

A method of measuring microbial activity of microbes in real time includes preparing a medium to enable microbial activity and placing the medium in operative contact with an appropriate sensor. The sensor is scanned to provide measurement electrical signals representative of position and amount of microbial activity, the sensor being responsive to a by-product of the microbial activity, such as a change in pH. The measurement signals can then be processed to provide a visual image display, and the display can visually distinguish between levels of pH activity and coordinate positions of the microbial activity.

4 Claims, 5 Drawing Sheets

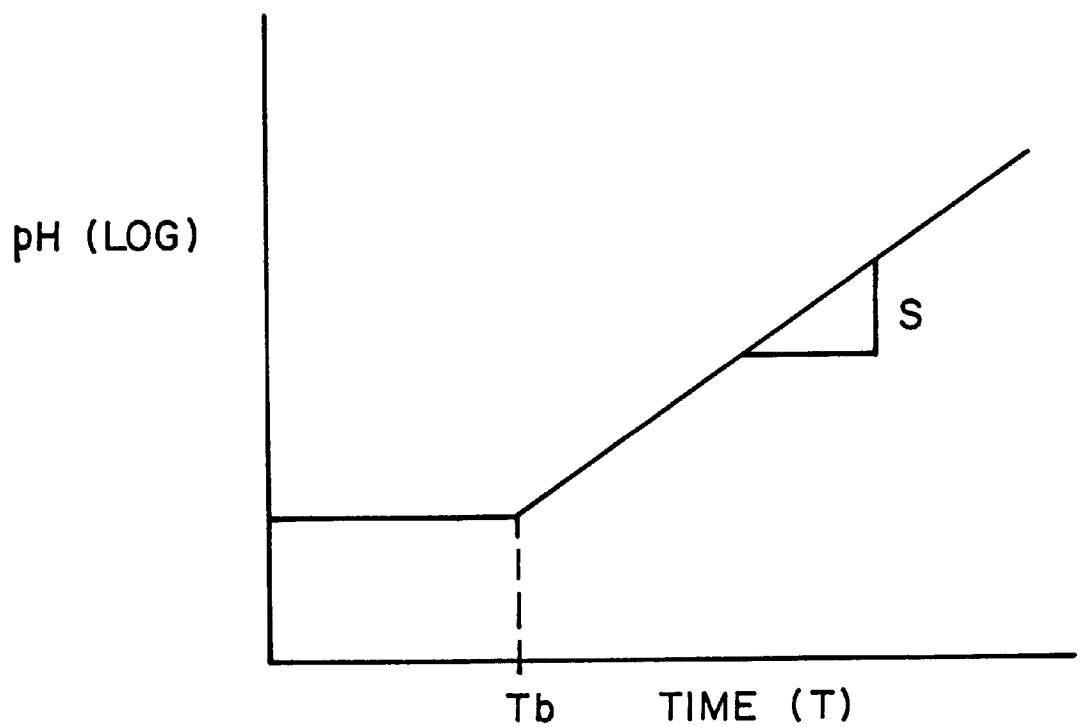

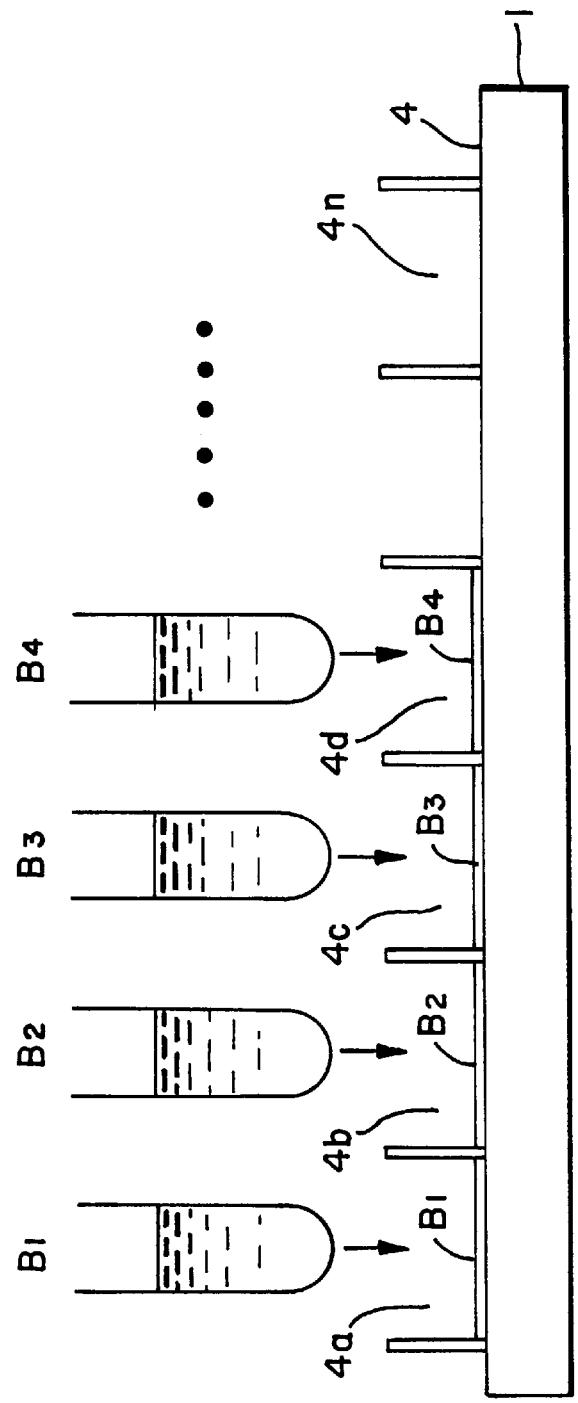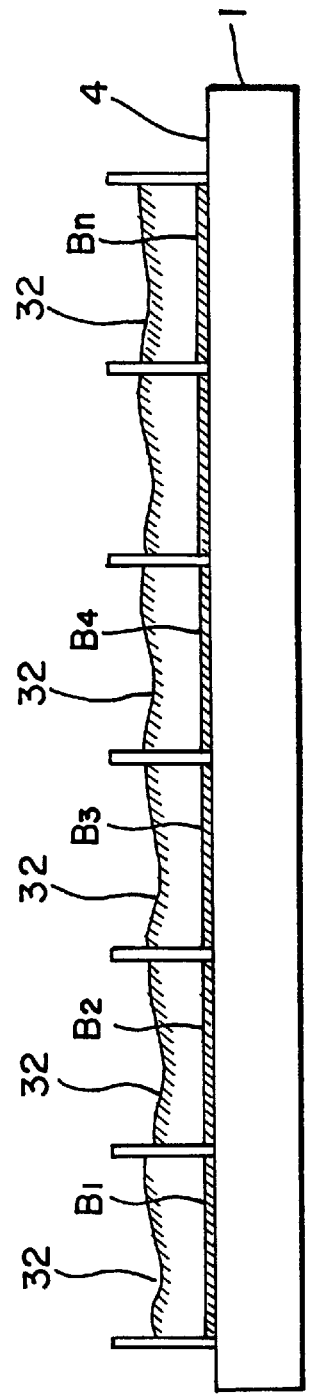

PROCESS FOR VISUALLY MEASURING A MICROBIAL ACTIVITY STATE DURING REAL TIME

BACKGROUND OF THE INVENTION

1. Field of the Invention

This invention relates to a process for measuring the state of microbial activities and more particularly a real time measurement with displayed images.

2. Description of Related Art

The controlled activities of microorganisms are extensively used in a wide variety of industrial fields, such as the brewing of liquors and wines, manufacturing of drugs, restoration of environmental pollution, etc. On the other hand, undesirable microorganisms do harm in various fields, such as causing many diseases or putrefying foods. In either case, it is essential to observe whether any microorganism exists or not, and if it does exist, how active it is.

In general to carry out the above-mentioned observation, microorganisms are actually applied to a process (for example, the brewing process) and an evaluation is made on whether the required effects are obtained or not, or microorganisms are incubated in a suitable culture medium and the results of propagation of microorganisms are determined.

However, in any of the above-mentioned cases, evaluations are made on the results in which microorganisms have already carried out some activities or microorganisms have finished their activities, and a considerable time is required to have the results, and it is not possible to evaluate the state of microbial activities in real time. Thus, there is still a need to improve the measurement of microbial action.

OBJECTS AND SUMMARY OF THE INVENTION

This invention is accomplished with the above-mentioned matters taken into account, and it is an object of this invention to provide a process for measuring the state of microbial activities which can be evaluated in real time.

In order to achieve the above-mentioned object, a process for measuring the state of microbial activities according to this invention (hereinafter simply called the "measuring method") is characterized by allowing microorganisms to work or incubating microorganisms in the process or environment in which the microorganisms are expected to work, and observing the change of chemical substances varied by the metabolism of microorganisms as two-dimensional images, as well as numerically identifying the activity state of the microorganisms based on image changes.

In actuality, it has become possible to directly observe the state of microbial activities without waiting for the final results by determining the change in chemical substances near the microorganism which are caused by metabolism of the microorganism, when the microorganism is placed under the active conditions, in the form of two-dimensional concentration distribution images.

That is, by incorporating the two-dimensional images in real time measurement, either of the following can be obtained.

(1) Ratio of concentration change in chemical substances to time at the point in which the chemical substance concentration is either the maximum or the minimum;

(2) Ratio of the change in the area to time by finding the area of the portion in which the chemical substance concentration is higher or lower than the specified value;

(3) Ratio of the total change to time by finding the total change in chemical substances; and (4) Ratio of propagation of one individual microorganism by counting the population of the portion in which the chemical substance concentration is higher or lower than the specified value.

These values serve as indices of a large or small metabolism of the microorganism, enabling the numerical evaluation of the degree of microbial activities.

Chemical substances varied by the microbial activities are measured using an optical scanning two-dimensional concentration distribution measuring apparatus. One of the optical scanning two-dimensional concentration distribution measuring apparatus is LAPS (Light-Addressable Potentiometric Sensor). The LAPS has recently been developed for the two-dimensional measurement of the Ph dissolved in the liquid or in the liquid soaked into the substance, and this kind of sensor substrate scans the semiconductor substrate forming a sensor surface reacting to ions, etc. with suitable light and measures the Ph by taking out the light current induced in the semiconductor substrate by this scanning, as described in "Improvement of Spatial Resolution of a Laser-Scanning pH-Imaging Sensor", Japan Journal of Applied Physics, Vol. 33 (1994), pages L394–L397, by Nakao et al. and incorporated herein by reference.

The distribution of concentration of the dissolved substance is measured by inserting the sensor surface of the equipment into the object to be directly measured or bringing it into contact with the object. The data obtained is computer-processed and outputted as a two-dimensional or three-dimensional concentration distribution image. It can trace not only the concentration distribution at a specified time, but also the condition of changes in real time. The images obtained in real time can easily be compared with electromagnetic wave images obtained visually or by CCD camera.

Examples of the above-mentioned chemical substances include various inorganic ions, organic ions, organic substances, substances related to enzyme reactions, substances related to antigen-antibody reaction, and substances related to inheritance, which dissolve in the liquid and are able to be measured by properly modifying the above-mentioned optical scanning two-dimensional concentration distribution measuring apparatus surface.

In addition, it is possible to compare the two-dimensional concentration distribution image with the electromagnetic wave image and to determine the correlationship between the concentration distribution of the chemical substance caused by the microorganism and the actual existing position of the microorganism.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 3 is a graph to illustrate an operation of the measurement procedure;

FIGS. 5A and 5B are views to illustrate a third embodiment.

DETAILED DESCRIPTION OF THE PREFERRED EMBODIMENTS

Figure 1:
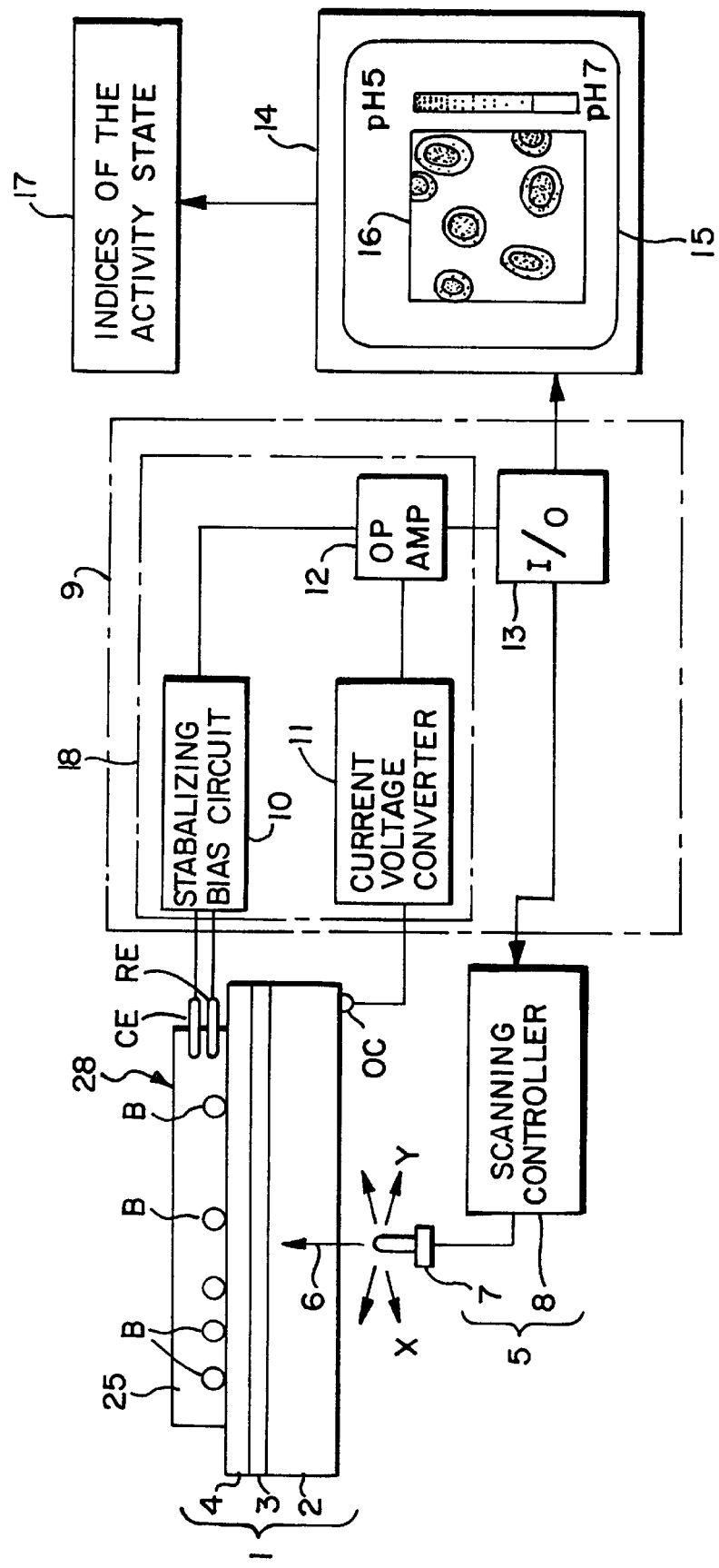
FIG. 1 is a schematic representation showing one example of an optical scanning two-dimensional concentration distribution measuring apparatus used in a measuring process according to this invention.

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide a process for measuring a microbial activity state.

Referring now to the drawings, the present invention will be described in detail hereinafter.

Embodiment 1

Referring now to FIGS. 1 and 2, an example in which the measuring process according to this invention is applied to a food manufacturing process, such as fermentation and brewing, is described. In the process in which microbial capabilities are utilized, the microorganism best suited must be chosen (screened), and the best-suited microorganism can be determined by applying the microorganism to the actual process and observing the activity state by the method described below. In this event, the substance changed by the metabolism of a microorganism is the hydrogen ion, and an optical scanning two-dimensional concentration distribution measuring apparatus, which is sensitive to pH, is used for the measurement.

That is, FIG. 1 schematically illustrates an optical scanning two-dimensional concentration distribution measuring apparatus used for implementing the measuring process according to this invention. In FIG. 1, numeral 1 is a sensor portion of the optical scanning two-dimensional concentration distribution measuring apparatus, and this sensor portion 1 comprises a $SiO_2$ layer 3 and a $Si_3N_4$ layer 4 successively formed on one surface (top surface in the illustrated example) of the substrate which comprises a semiconductor, such as silicon, etc. by thermal oxidation, CVD, or other technique and is formed to respond to hydrogen ions. And CE and RE are a counter electrode and a reference electrode, respectively, installed above the $Si_3N_4$ layer 4, which is the sensor surface, and are connected to the potentiostat 18, to be discussed later, to apply a voltage. OC is an ohmic electrode or working electrode installed on the semiconductor substrate 2 for taking out current signals, and is connected to a potentiostat 18 which includes a stabilizing bias circuit 10, a current-voltage converter 11 and an operational amplifier circuit 12, to be discussed later.

Numeral 5 is a light irradiating portion for irradiating the semiconductor substrate 2 of the sensor portion 1 and is installed on the bottom surface side (opposite to the sensor surface 4) of the semiconductor substrate 2, and comprises a laser beam source 7 for intermittently emitting the light adjusted to provide an optimum beam diameter by control signals from a computer 15, later discussed, via an interface board 13, later discussed, as probe light 6 and a scanning controller 8 for controlling the laser beam source 7 to scan in the two-dimensional directions (X and Y directions in the figure).

Numeral 9 is a control box for controlling the sensor portion 1 and the light irradiating portion 5 and comprises the potentiostat 18 for applying suitable bias voltage to the semiconductor substrate 2, the stabilizing bias circuit 10, the current-voltage converter 11 for converting current signals taken from the ohmic electrode OC formed on the semiconductor substrate 2 to voltage signals, the operational amplifier circuit 12 to which signals from this current-voltage converter 11 are inputted, and the interface board 13 for exchanging signals with this operational amplifier circuit 12 or outputting control signals to the scanning controller 8.

Numeral 14 is the computer as a control unit and a processor for carrying out various controls and computations, which is equipped with image processing capabilities, and numeral 15 is a display for displaying the pH concentration distribution. As noted on the display 15, the actual images 16 representative of the position and concentration of the pH distribution is generated from the current flow contemporaneously with the X, Y position of the scanning laser beam in real time. The rings are indicative of different levels of pH and, for example, could be color coded. Display 15 also provides a pH scale to correlate the level of pH relative to the video images. Thus, the content and position of the visual images, as displayed in real time, enable the operator to practice different methods of evaluating the activity of specific microorganisms by observing the changes in pH rather than counting the number of microorganisms. By visualizing two-dimensional concentration distribution images of a chemical concentration (for example, pH), the operator can readily determine, in an economical manner, the state of microbial activities.

Figure 2A:
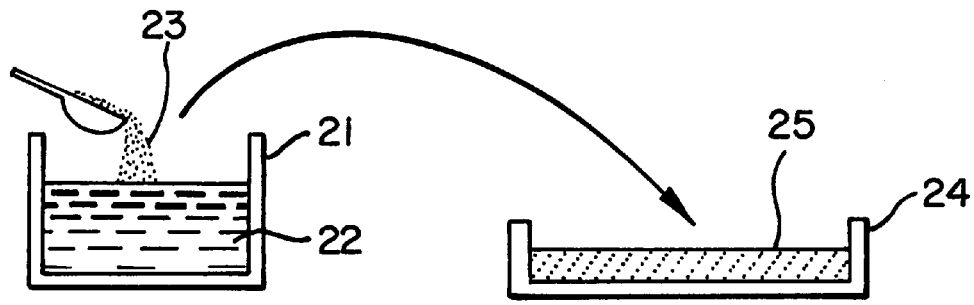
FIGS. 2A, 2B, and 2C are views to illustrate a first embodiment.
Figure 2B:
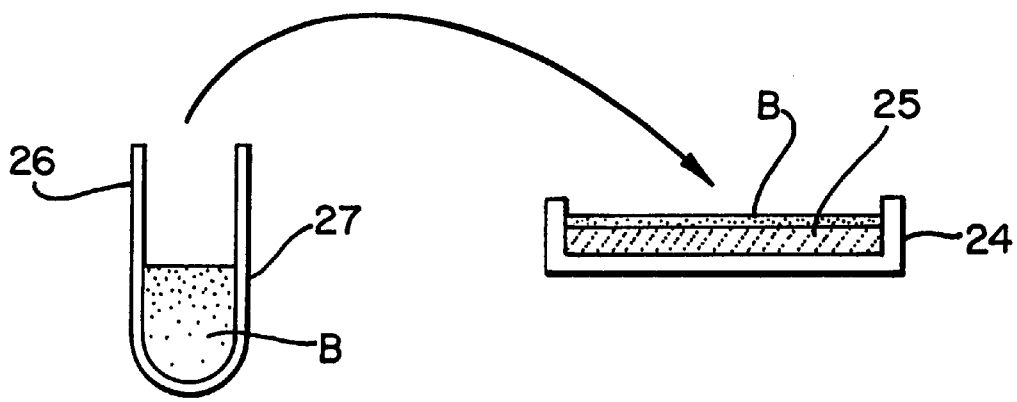

The sample used in this measuring process according to this invention is formed by a generally used method and, for example, a sample of agar culture medium is formed. This method is described, for example, in the microbial inspection (Encyclopedia of Clinical Inspection Technique 7, published by Igaku Shoin). For an applicable process, as shown in FIG. 2(A), agar 23 is added to a solution 22 adjusted to a condition suitable for microbial activities in a suitable container 21, is housed in a Petri dish 24 and is designated as gel 25. On the other hand, as shown FIG. 2(B), the microorganism B to be evaluated in the test tube 26 is diluted with a suitable diluent 27, and this diluted microorganism B is applied to the surface of the gel 25, housed in the Petri dish 24 to have a sample 28.

Figure 2C:
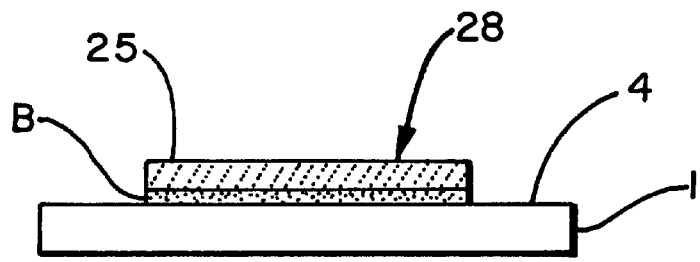

As shown in FIG. 2(C), sample 28 is turned upside down and placed on the sensor surface 4 of the optical scanning sensor portion 1 of the two-dimensional concentration distribution measuring apparatus, the environmental temperature is properly set, and incubation of microorganism B takes place.

In the above optical scanning two-dimensional concentration distribution measuring apparatus, the counter electrode CE and the reference electrode RE are inserted into the gel 25 of the sample 28 and direct current voltage from the potentiostat 18 is applied across the reference electrode RE and the ohmic electrode OC so as to generate a depletion layer in the semiconductor substrate 2, and specified bias voltage is applied to the semiconductor substrate 2. The semiconductor substrate 2 with is irradiated with a probe light 6 intermittently at given intervals (for example, 10 kHz) so that an alternate current optical current is generated in the semiconductor substrate 2. The intermittent frequency of the light scan can remove background noise from the signal.

In addition, by moving the light irradiating portion 7 in an X or Y direction, the semiconductor substrate 2 is irradiated with the probe light 6, as if it is scanned in the two-dimensional direction and a two-dimensional image 16 indicating pH can be displayed on the screen of the display 15 of the computer 14 by the positional signal (X, Y) at the sample 28 and the alternate current optical current value observed at the position.

Then, the pH value at the incubation start point is recorded (in this event, at sample 28, pH distribution is not observed) and incubation takes place. The place where the first pH value change occurs after the start of incubation is designated as the pH measuring point, and the pH value at the measuring point is recorded at regular intervals, and the difference of the pH value at the start of incubation and after incubation takes place is measured and recorded at regular intervals. The difference of the pH values tend to increase logarithmical with respect to time. FIG. 3 shows the relationship between the pH value and the time in this event, with time taken as abscissa and the pH value as ordinate (displayed in logarithmic scales), respectively. Let the time until then be $T_4$ and the logarithmic value of the increment per unit time of the pH value when the pH value increases logarithmically with respect to time be S, these values $T_4$ and S are indices 17 of the activity state (see FIG. 1). That is, when several species of microorganism B are screened with the activity conditions of microorganism B set constant, the microorganism with a smaller $T_4$ and a larger S provides capabilities to more efficiently carry out the intended process.

The above-mentioned process is an example in which the activity conditions of microorganism B are set constant and activities of a plurality of microorganism B species are evaluated for screening, but the same technique can be used when the optimum conditions are determined to carry out the process with respect to microorganism B, chosen by screening. However, in this event, $T_4$ and S should be compared, respectively, with the specie of microorganism set constant while gel sample conditions and process conditions are varied.

In the above-mentioned example, there may be a case in which the pH value change first occurs at a plurality of points. In this event, an optional point may be designated as a pH value change observation point and several or all points of them may be designated as pH value change observation points. Which point to adopt must be determined and the observation points should be set constant in a series of screening or investigation of activity conditions.

The above-mentioned embodiment is an example in which the present invention is applied to a food manufacturing process, such as fermentation and brewing, but it is needless to say that it can be applied to other processes which utilize capabilities of microorganism B.

Embodiment 2

In this embodiment, as an index of the activity state of microorganism B, the ratio of increase in population of microorganism B is used. As in the case of Embodiment 1, an incubation of microorganism B is allowed to take place and two-dimensional concentration distribution images of a chemical substance discharged are successively obtained. The chemical substance measured is a hydrogen ion, as that in Embodiment 1, but may be any other chemical substances.

Figure 4A:
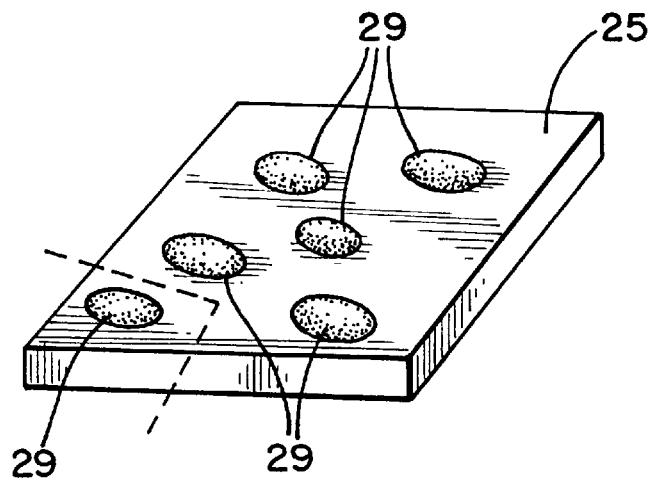
FIGS. 4A and 4B are views to illustrate a second embodiment.

Microorganism B increases in population as incubation takes place for a specified time period and forms a colony 29 of several individuals (microorganism B) aggregate, as shown in FIG. 4(A). Because around this colony 29, the pH value differs from that at the start of the incubation, this can be easily identified by observing the two-dimensional concentration distribution images.

Figure 4B:
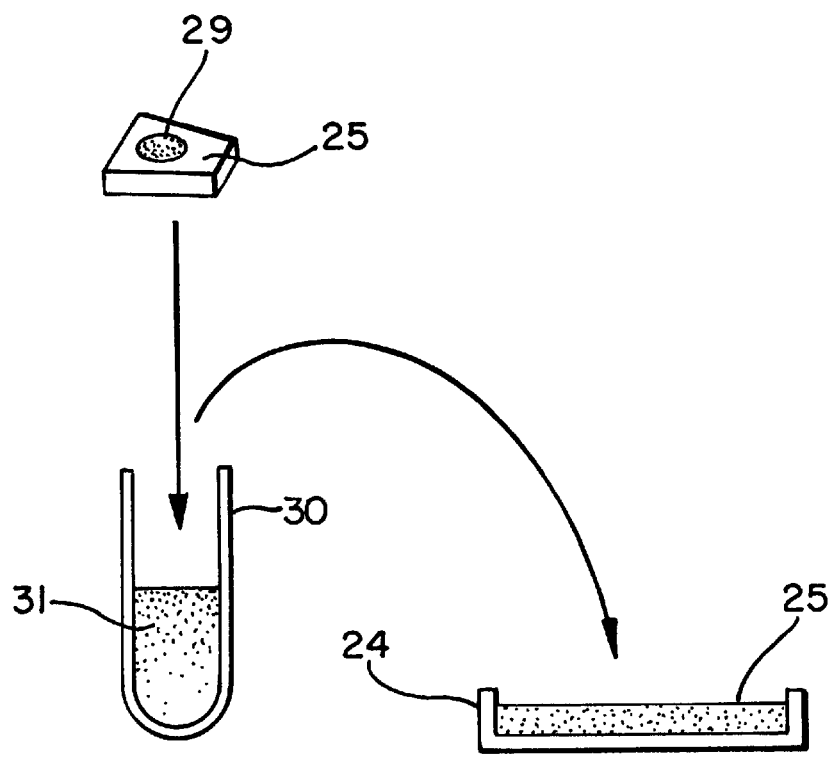

As described above, colony 29 is formed in a plurality, and therefore, one of each of them is cut for each gel 25, as shown in the conceptual line in FIG. 4(A) at regular intervals. The cut colony 29 is dissolved in the culture liquid 31 in the test tube 30 and is isolated into one individual microorganism B, as shown in FIG. 4(B). Again, as in the method described above, it is fixed to the sensor surface 4 of the optical scanning sensor portion 1 of the two-dimensional concentration distribution measuring apparatus and incubated.

Each of the isolated microorganisms B repeats multiplication and forms colonies. Because around the colony, the pH value differs from that at the start of incubation, it can be easily identified by observing the two-dimensional concentration distribution images and this time, the total number of the colonies can be determined. This total number of colonies corresponds with the number of microorganisms B in the colony cut together with the gel before and indicates the number of individuals multiplied since it is cut.

Now it is possible to know how one individual of a microorganism increases the population as time passes by carrying out the initial microorganism incubation and the cutting of the colony at regular intervals and determining the number of microorganisms in the colony. The increase of population becomes logarithmic after a specified time (for example, $T_b$'), and letting the logarithmic value of the then-increment be S', the microorganism with a smaller $T_b$' and a larger S' can be regarded as the microorganism which provides the capabilities to efficiently carry out the intended process, and therefore, using these values, the screening and optimum activity conditions of microorganism B can be obtained.

Embodiment 3

In this embodiment, a description is made on an application example in which soils contaminated by crude oil, leaking from tankers, petroleum plants, etc. due to accidents or other petroleum waste, are decontaminated with a microbial agent. The contamination varies in forms and requires a more suitable screening of microorganism B and a quick determination of the conditions in which the microorganism B is allowed to be active to the maximum. The specific application method is described as follows.

In this embodiment, the measured chemical substance is also hydrogen ion, but various types of ion species and organic substances may be acceptable. For the measuring equipment, an optical scanning two-dimensional concentration distribution measuring apparatus which is induction-reactive to hydrogen ions is used, but is needless to say that the optical scanning two-dimensional concentration distribution measuring apparatus with the sensor surface 4, modified with suitable induction-reacting substances in accord with chemical substances to be measured, is used.

In this embodiment, as shown in FIG. 5(A), the sensor surface 4 is divided into several measuring zones $4a$, $4b$, $4c$, $4c$, ..., $4n$ so that several types of candidate microorganisms B can be simultaneously evaluated, and in the relevant measuring zones $4a$–$4n$, different microorganisms $B_1$, $B_2$, $B_3$, $B_4$, ... $B_n$ (not illustrated) are incubated, and their activity state is observed. After each of the microorganisms $B_1$–$B_n$ is diluted with a suitable solution, it is applied to each of the measuring zones $4a$–$n$ and thereafter, the placement of the soil 32 to be decontaminated on each zone, as shown in FIG. 5(B), can fix the relevant microorganisms $B_i$–$B_n$. Any measurement after this stage should be carried out in the same manner as in Embodiment 1.

The measurement can be made in the same manner not only in screening of the optimum microorganism B, but also in the process of determining the conditions in which the screened microorganism B can perform from being inactive to having the maximum activity. However, in this event, the same microorganism B should be applied to each of the measuring zones $4a$–$4n$, and nutrients, etc. added to each of the measuring zones $4a$–$4n$ should be properly varied.

Instead of placing the soil 32 which is to be decontaminated on the sensor surface 4, screening is possible by directly embedding the sensor portion 1 with each of the microorganisms $B_1$–$B_n$ applied to the soil to be decontaminated.

Embodiment 4

All of the above-mentioned embodiments describe the manner in which the chemical substance to be changed by the metabolism of microorganism B is hydrogen ion, but instead of this substance, the change of, for example, various inorganic ions, such as calcium ions, etc., organic acids, such as lactic acid, etc., and other various chemical substances can also be observed. In this case, the sensor surface 40 of the sensor portion 1 of the optical scanning two-dimensional concentration distribution measuring apparatus should be modified with the substance which responds selectively to the substance observed.

Embodiment 5

In this embodiment, the manner in which the existence of harmful microorganisms is found is described. The sample used in this method is generally a used sample, and, for example, a sample of agar culture medium is formed. This method is described, for example, in the microbial inspection (Encyclopedia of Clinical Inspection Technique 7, published by Igaku Shoin).

That is, as in Embodiment 1, the change in the chemical substance is observed as two-dimensional concentration distribution images at regular intervals as soon as incubation begins to take place.

Examples of the chemical substances to be measured include any chemical substances, including hydrogen ions. If any microorganism exists, continuing incubation for a specified time allows the microorganism to increase the population and form colonies in which several individuals aggregate. Because the concentration of a chemical substance differs around this colony from that at the start of the incubation, the change in the chemical substance can quickly and easily be identified by two-dimensional concentration distribution images.

With the above-mentioned two-dimensional concentration distribution images, it is not only possible to confirm the existence of a microorganism, but also to identify the portion of interest, such as at which portion on the culture medium the microorganism exists and, in addition, in which portion of the microorganism the change in concentration of a chemical substance is generated, that is, to identify the correlation between the chemical information and the physical information, based on the actual images (electromagnetic wave images), obtained visually or by CCD camera. In particular, the calcium ions or lactic acid ions are substances frequently found in the vital reaction, and the measuring process according to this invention can be applied not only to the process, effectively utilizing the microorganism B, but also to research on vital reactions, etc.

Additionally, in the above-mentioned optical scanning two-dimensional concentration distribution measuring apparatus, a probe light 6 is designed to be irradiated from the rear surface side (opposite to the sensor surface 4) of the semiconductor substrate 2, but in lieu of this, it may be designed to be irradiated from the sensor surface 4 side.

As described above, the process of this invention enables an easy, quick, and real-time evaluation of the activity state of the microorganisms, such as whether the microorganism exists or not, and if it does exist, how active it would be. Consequently, it is possible to quickly and easily carry out the screening the an optimum microorganism in various processes in which microorganisms are utilized, as well as to determine the optimum activity conditions of the microorganism. This also enables a quick determination of the existence of harmful microorganisms.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A method for determining an activity of microorganism growth by measuring the concentration of a byproduct chemical species inherent in the growth of the microorganism with a pH electrode, said method comprising:

placing a sample of the microorganism in a medium;

placing the medium in operational contact with a semiconductor optical scanning two-dimensional concentration distribution measuring sensor assembly;

irradiating the semiconductor sensor assembly with an oscillating light source while the sensor assembly is in contact with the medium to optically scan the semiconductor sensor assembly in an X- and Y-direction to provide an electric current that is induced by an incident scanning light;

applying a biasing voltage to the semiconductor sensor assembly;

measuring the current at discrete positions along the semiconductor sensor assembly, and interpreting the electric current in terms of a concentration of pH of said byproduct chemical species as it effects the light induced current, contemporaneous with said irradiation of said semiconductor sensor assembly;

repeating the irradiating and measuring steps to determine changes of pH at the discrete positions along the semiconductor sensor and generating the indices of the activity of microorganism state of growth with a potentiostat based on the plurality of measurements; and displaying the concentration of said byproduct chemical species as a two dimensional image.

2. The method of claim 1 further including measuring the size of the visual image to determine the extent of microbe activity.

3. The method of claim 1 wherein the pH activity is displayed as the visual image along with a pH scale.

4. The method of claim 3 wherein different levels of pH are color-coded in the displayed images.

* * * * *